United States Patent [19]
Winter et al.

[11] Patent Number: 4,831,134

[45] Date of Patent: May 16, 1989

[54] N-HYDROXY HINDERED AMINE STABILIZERS

[75] Inventors: Ronald A. E. Winter, Armonk; James P. Galbo, Hartsdale, both of N.Y.

[73] Assignee: Ciba-Geigy Corporation, Ardsley, N.Y.

[21] Appl. No.: 99,418

[22] Filed: Sep. 21, 1987

[51] Int. Cl.$^4$ .................. C07D 401/04; C07D 401/14
[52] U.S. Cl. .................................... 540/524; 546/187; 546/188; 546/189; 546/225; 546/242; 546/221; 524/98; 524/99; 524/100; 524/102

[58] Field of Search .................. 546/19, 20, 188, 187, 546/189, 225, 242; 544/194, 207, 231, 357, 360; 540/488, 524

[56] References Cited

U.S. PATENT DOCUMENTS 4,691,015  9/1987  Behrens et al. ........................ 546/19

*Primary Examiner*—Robert T. Bond
*Attorney, Agent, or Firm*—Harry Falber

[57] ABSTRACT

1-Hydroxy-2,2,6,6,-tetraalkylpiperidine derivatives are effective as light stabilizers in a variety of substrate systems.

10 Claims, No Drawings

N-HYDROXY HINDERED AMINE STABILIZERS

BACKGROUND OF THE INVENTION

The invention relates to novel polyalkylpiperidine derivatives exhibiting an OH group on the hindered nitrogen atom of the piperidine ring and a diversity of substituents on the 4-position of the ring.

Various N-hydroxy derivatives of hindered amines are known. For example, a substantial number of such derivatives are generically disclosed in U.S. Pat. No. 4,590,231. The substituents on the 4-position include ether, ester, amino, dioxaspiro, diaza-dione, urea and triazine substituents, among others. These derivatives are identified as stabilizers in polyolefin compositions. Mono- and di-piperidinyl ester derivatives are likewise disclosed in Japanese 54-69162 for use in stabilizing urethane polymers. Other N-hydroxy derivatives are disclosed in Chemical Abstracts 74, 64180u (1971); J. Poly. Sci., Polymer Chem. Ed. 22, 227-81 (1984); Polym. Sci. Technol. 26, 35-47 (1984); and Zh. Org. Khim. 6, 2365-9 (1970); as well as in U.S. Pat. No. 3,936,456, U.S. Pat. No. 4,404,302 and U.S. Pat. No. 4,472,547.

Accordingly, it is the object of the instant invention to identify a series of new N-hydroxy hindered amines having a broad range of stabilization performance characteristics.

These derivatives thus correspond to the formula

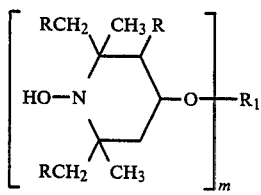

(A)

wherein
R is hydrogen or methyl;
m is 1-4;
when m is 1, $R_1$ is

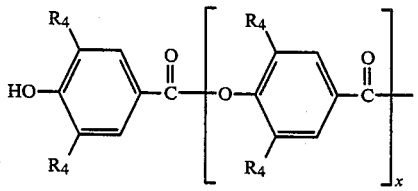

where x is 0 or 1 and $R_4$ independently are $C_1$–$C_8$ alkyl, or

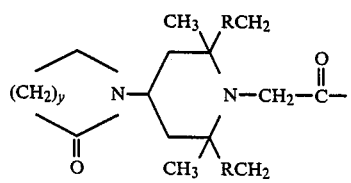

with y is 2-4;
when m is 2, $R_1$ is

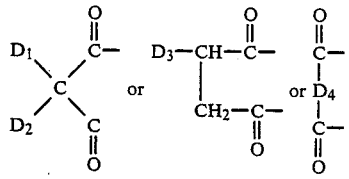

wherein $D_1$ and $D_2$ are independently $C_1$–$C_8$ alkyl, $C_6$–$C_{10}$ aryl, $C_7$–$C_{12}$ aralkyl or 3,5-di-t.butyl-4-hydroxybenzyl and $D_2$ is also hydrogen, $D_3$ is $C_1$–$C_{18}$ alkyl or $C_2$–$C_{18}$ alkenyl, and $D_4$ is $C_5$–$C_{12}$ cycloalkylene;

when m is 3, $R_1$ is a trivalent acyl radical of an aliphatic, unsaturated aliphatic, cycloaliphatic or aromatic tricarboxylic acid;

when m is 4, $R_1$ is a tetravalent acyl radical of a saturated or unsaturated aliphatic or aromatic tetracarboxylic acid;

In the formula, representative alkyl groups include methyl, ethyl, n-propyl, n-butyl, tert-butyl, n-hexyl, n-octyl, 2-ethylhexyl, n-undecyl and n-dodecyl; aryl includes phenyl and naphthyl; aralkyl includes benzyl, alpha-methylbenzyl and phenethyl; and alkenyl includes 1-propenyl, allyl, methallyl, 2-butenyl, 2-hexenyl and 2-octenyl. $R_1$ as a trivalent acyl radical is, for example, an acyl radical of benzene-1,2,4-tricarboxylic acid. $R_1$ as a tetravalent acyl radical is, for example, an acyl radical of 1,2,3,4-butanetetracarboxylic acid, 1,2,3,4-but-2-enetetracarboxylic acid and 1,2,3,5- and 1,2,4,5-pentanetetracarboxylic acid. In the $R_1$ members when m is 2, malonates are preferred where $D_1$ is lower alkyl and $D_2$ is hydrogen or lower alkyl.

The hydroxylamine derivatives of this invention are generally prepared by oxidizing the corresponding N-H hindered amine with an appropriate peroxy compound such as hydrogen peroxide or tert-butyl hydroperoxide in the presence of molybdenum oxide or a metal carbonyl or metal oxide catalyst followed by reduction of the oxyl intermediate formed thereby to the desired N-hydroxy derivative, preferably by catalytic hydrogenation. Molybdenum (VI) is noted to increase the efficiency of the oxidation step. The reaction is preferably conducted in hydrocarbon solvents such as toluene. The starting materials needed to prepare the derivatives of this invention are items of commerce or can be prepared by known methods.

The derivatives are particularly effective in stabilizing organic materials primarily against the degradative effects of actinic stimuli. Such organic materials include polyolefins, vinyl chloride polymers, elastomers, polyesters and polyurethanes. They are particularly applicable for the stabilization of ambient cured and acid catalyzed thermoset coatings or enamels wherein they improve the durability and weatherability of the ambient cured systems and wherein they do not inhibit or interfere with cure in acid catalyzed systems in view of their reduced basicity.

The following examples illustrate the embodiments of this invention.

EXAMPLE 1

Di-(1-hydroxy-2,2,6,6-tetramethylpiperidin-4-yl)methylmalonate

A 4.5M solution of t-butyl hydroperoxide in toluene (25 ml, 113 mmol) is rapidly added to a mixture of 50.0 g (126 mmol) of di-(2,2,6,6-tetramethylpiperidin-4- yl)methylmalonate, 3.0 g of molybdenum trioxide, and 100 ml of toluene at 90° C. Another portion of 4.5M t-butyl hydroperoxide in toluene (87 ml, 392 mmol) is added over 20 minutes. The reaction mixture is stirred for 3 hours at 85°–90° C., then cooled and filtered. The filtrate is concentrated and crystallized from methanol to yield 20.5 g (38%) of di-(1-oxyl-2,2,6,6-tetramethylpiperidin-4-yl)methylmalonate, an orange solid, m.p. 111°–120° C.

A mixture of 20.3 g (47.6 mmol) of di-(1-oxyl-2,2,6,6-tetramethylpiperidin-4-yl)methylmalonate, 1.0 g of 5% palladium on carbon, and 100 ml of dichloromethane is hydrogenated in a Paar apparatus (50 psi, ambient temperature). The catalyst is then filtered off, and the filtrate is diluted with heptane (50 ml). The dichloromethane-heptane solution is fractionally distilled (bath temperature 50° C.) until the product begins to crystallize, then cooled and filtered to give 11.9 g (58% yield) of the title compound, as a white crystalline solid, m.p. 153°–55° C.

Anal. Calcd. for $C_{22}H_{40}N_2O_6$: C, 61.7; H, 9.4; N, 6.5. Found: C, 61.5; H, 9.2; N, 6.6.

The compounds in the following examples are prepared according to the procedure of Example 1 utilizing the appropriate starting materials.

EXAMPLE 2

Di-(1-hydroxy-2,2,6,6-tetramethylpiperidin-4-yl)n-butylmalonate m.p. 92°–93° C.

Anal. Calcd. for $C_{25}H_{46}N_2O_6$: C, 63.8; H, 9.9; N, 5.9. Found: C, 63.9, H, 9.8; N, 6.0.

EXAMPLE 3

Di-(1-hydroxy-2,2,6,6-tetramethylpiperidin-4-yl)diethylmalonate m.p. 115°–118° C.

Anal. Calcd. for $C_{25}H_{46}N_2O_6$: C, 63.8, H, 9.9; N, 5.9. Found: C, 63.9; H, 10.0; N, 5.9.

EXAMPLE 4

1-Hydroxy-2,2,6,6-tetramethylpiperidin-4-yl 4-(4-hydroxy-3,5-di-tert-butylbenzoyloxy)-3,5-di-tert-butylbenzoate m.p. 170°–2° C.

Anal. Calcd. for $C_{39}H_{59}NO_6$: C, 73.5; H, 9.3; N, 2.2. Found: C, 72.7; H, 9.2; N, 2.3.

EXAMPLE 5

1-Hydroxy-2,2,6,6-tetramethylpiperidin-4-yl[4-(2-oxoazepin-1-yl)-2,2,6,6-tetramethylpiperidin-4-yl]acetate m.p. 251°–2° C.

Anal. Calcd. for $C_{26}H_{47}N_3O_4$: C, 67.1; H, 10.2; N, 9.0. Found: C, 67.1; H, 9.9; N, 8.9.

EXAMPLE 6

Di-(1-hydroxy-2,2,6,6-tetramethylpiperidin-4-yl)2-(4-hydroxy-3,5-di-tert-butylbenzyl)-2-n-butylmalonate m.p. 148°–52° C.

Anal. Calcd. for $C_{40}H_{68}N_2O_7$: C, 69.7; H, 9.9; N, 4.1. Found: C, 69.9; H, 10.0, N, 4.2.

EXAMPLE 7

Tetrakis(1-hydroxy-2,2,6,6-tetramethyl-4-piperidyl)1,2,3,4-butane-tetracarboxylate m.p. 201°–4° C.

Anal. Calcd. for $C_{44}H_{78}N_4O_{12}$: C, 61.8; H, 9.2; N, 6.5. Found: C, 61.5; H, 9.2; N, 6.4.

EXAMPLE 8

Di-(1-hydroxy-2,2,6,6-tetramethylpiperidin-4-yl)trans-1,4-cyclohexane-dicarboxylate m.p. 185°–192° C.

Anal. Calcd. for $C_{26}H_{46}N_2O_6$: C, 64.7; H, 9.6; N, 5.8. Found: C, 64.3; H, 9.4; N, 5.6.

Summarizing, this invention is seen to provide a series of new N-hydroxy substituted hindered amine stabilizers. Variations may be made in proportions, materials and procedures without departing from the scope of the invention as defined by the following claims.

What is claimed is:

1. A compound corresponding to the formula $$\left[ \begin{array}{c} RCH_2 \quad CH_3 \quad R \\ HO-N \diagup \diagdown O-R_1 \\ RCH_2 \quad CH_3 \end{array} \right]_m$$

wherein
R is hydrogen or methyl;
m is 1–4;
when m is 1, $R_1$ is

[structure: HO—(aromatic ring with $R_4$ substituents)—C(O)—[O—(aromatic ring with $R_4$ substituents)—C(O)—]$_x$]

x is 0 or 1 and $R_4$ independently are $C_1$–$C_8$ alkyl, or

[structure: (CH$_2$)$_y$—N(C=O)—piperidine ring—N—CH$_2$—C(O)—]

with y is 2–4;
when m is 2, $R_1$ is

[structure with D$_1$, D$_2$, D$_3$, D$_4$ substituents and carbonyl groups]

wherein $D_1$ and $D_2$ are independently $C_1$–$C_8$-alkyl, $C_6$–$C_{10}$-aryl, $C_7$–$C_{12}$-aralkyl or 3,5-di-t.-butyl-4-hydroxybenzyl and $D_2$ is also hydrogen, $D_3$ is $C_1$–$C_{18}$-alkyl or $C_2$–$C_{18}$-alkenyl, and $D_4$ is $C_5$–$C_{12}$-cycloalkylene;

when m is 3, $R_1$ is a trivalent acyl radical of a benzene-tricarboxylic acid;

when m is 4, $R_1$ is a tetravalent acyl radical of 1,2,3,4-butanecarboxylic acid, 1,2,3,4-but-2-enetetracarboxylic acid, 1,2,3,5-pentanetetracarboxylic acid or 1,2,4,5-pentanetetracarboxylic acid.

2. The compound of claim 1, wherein m is 2, $R_1$ is

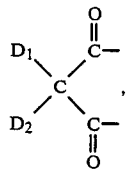

$D_1$ is $C_1$–$C_8$-alkyl or 3,5-di-t.butyl-4-hydroxybenzyl and $D_2$ is $D_1$ or hydrogen.

3. Di-(1-hydroxy-2,2,6,6-tetramethylpiperidin-4-yl)methylmalonate according to claim 2.

4. Di-(1-hydroxy-2,2,6,6-tetramethylpiperidin-4-yl)n-butylmalonate according to claim 2.

5. Di(1-hydroxy-2,2,6,6-tetramethylpiperidin-4-yl)diethylmalonate according to claim 2.

6. 1-Hydroxy-2,2,6,6-tetramethylpiperidin-4-yl) 4-(4-hydroxy-3,5-di-tert-butylbenzoyloxy)-3,5-di-tert-butylbenzoate according to claim 1.

7. 1-Hydroxy-2,2,6,6-tetramethylpiperidin-4-yl[4-(2-oxoazepin-1-yl)-2,2,6,6-tetra-methylpiperidin-4-yl]acetate according to claim 1.

8. Di-(1-hydroxy-2,2,6,6-tetramethylpiperidin-4-yl)2-(4-hydroxy-3,5-di-tert-butyl benzyl)-2-n-butylmalonate according to claim 2.

9. Tetrakis(1-hydroxy-2,2,6,6-tetra-methyl-4-piperidyl)1,2,3,4-butane-tetracarboxylate according to claim 1.

10. Di-(1-hydroxy-2,2,6,6-tetramethylpiperidin-4-yl)trans-1,4-cyclohexane dicarboxylate according to claim 1.

* * * * *